United States Patent [19]

Uekusa et al.

[11] Patent Number: 5,178,835
[45] Date of Patent: Jan. 12, 1993

[54] BIOCHEMICAL ANALYSIS APPARATUS

[75] Inventors: Tadashi Uekusa; Takashi Koizumi; Yukihide Miyata, all of Kanagawa, Japan

[73] Assignee: Fuji Photo Film Co., Ltd., Kanagawa, Japan

[21] Appl. No.: 620,447

[22] Filed: Dec. 3, 1990

Related U.S. Application Data

[63] Continuation of Ser. No. 246,047, Sep. 19, 1988, abandoned.

[30] Foreign Application Priority Data

Sep. 18, 1987 [JP] Japan .................. 62-234292
Feb. 24, 1988 [JP] Japan .................. 63-41711

[51] Int. Cl.⁵ .......................................... G01N 21/00
[52] U.S. Cl. ............................ 422/66; 422/63; 436/44
[58] Field of Search ............ 422/58, 63, 66; 436/44, 436/46

[56] References Cited

U.S. PATENT DOCUMENTS

| | | | |
|---|---|---|---|
| Re. 31,149 | 2/1983 | Ginsberg et al. | 422/64 |
| 3,526,480 | 9/1970 | Findl et al. | 422/66 |
| 3,554,700 | 1/1971 | Maxon | 436/44 |
| 4,152,390 | 5/1979 | Nosco et al. | 422/63 |
| 4,298,571 | 11/1981 | DiFulvio et al. | 422/65 |
| 4,512,952 | 4/1985 | Blanding et al. | 422/66 |
| 4,647,431 | 3/1987 | Sekine et al. | 436/46 |
| 4,795,613 | 1/1989 | Azuma et al. | 436/46 |
| 5,004,582 | 4/1991 | Miyota et al. | 422/56 |

Primary Examiner—Robert J. Warden
Assistant Examiner—Theresa A. Trembley
Attorney, Agent, or Firm—Sughrue, Mion, Zinn, Macpeak & Seas

[57] ABSTRACT

A biochemical analysis apparatus for applying a liquid sample onto a long test film, incubating the sample-applied film portion by an incubator, and measuring the degree of color formation at the sample-applied portion comprises a cutter provided upstream from the position of sample application for cutting the long test film to a length necessary for a single step of sample application, and a cut-film conveyor for conveying the sample-applied and cut portion of the long test film into the incubator, whereby the long test film is utilized efficiently and processing thereof is facilitated.

8 Claims, 5 Drawing Sheets

BIOCHEMICAL ANALYSIS APPARATUS

This is a continuation of application Ser. No. 07/246,047 filed Sep. 19, 1988 now abandoned.

BACKGROUND OF THE INVENTION

1. Field of the Invention

This invention relates to a biochemical analysis apparatus for applying a liquid sample to a test film provided with a single reagent layer or a plurality of reagent layers, maintaining the test film at a predetermined temperature (i.e. carrying out incubation) for a predetermined time, and measuring the degree of color formation given rise to by a reaction of the reagent with the liquid sample during or after the incubation. This invention particularly relates to a biochemical analysis apparatus suitable for quick processing.

2. Description of the Prior Art

Qualitative or quantitative analysis of a specific chemical constituent in a liquid sample is generally conducted for various industrial purposes. Particularly, it is very important in biochemical and clinical fields to quantitatively analyze chemical constituents or physical constituents in body fluid such as blood or urine.

In recent years, as disclosed in, for example, Japanese Patent Publication No. 53(1978)-21677 and Japanese Unexamined Patent Publication No. 55(1980)-164356, there has been developed and put into practice a dry type chemical analysis slide for quantitatively analyzing a specific chemical constituent or a specific physical constituent contained in a liquid sample simply by applying a droplet of the liquid sample. With the chemical analysis slide, it is possible to analyze a liquid sample more simply and more quickly than with the conventional wet type analysis method. Therefore, the use of the chemical analysis slide is desirable particularly in medical organizations, research laboratories, or the like where many samples are to be analyzed.

In order to analyze a chemical constituent or the like contained in a liquid sample by use of the chemical analysis slide, a measured amount of the liquid sample is put on the chemical analysis slide and is maintained at a predetermined temperature (i.e. incubated) for a predetermined time in an incubator to cause a color reaction. The chemical analysis slide is then exposed to measuring light having a wavelength selected in advance in accordance with the combination of the constituent of the liquid sample with a reagent contained in the reagent layer of the chemical analysis slide, and the light reflected by the chemical analysis slide is measured in terms of the optical reflective density (hereinafter referred to simply as "optical density"). In this manner, quantitative analysis of the chemical constituent or the like is carried out.

In the medical organizations, research laboratories or the like in which many liquid samples are to be analyzed, it is desirable that the analysis be conducted automatically and sequentially. To satisfy this need, there have been proposed various chemical analysis apparatuses for carrying out sample analysis automatically and sequentially by use of the aforesaid chemical analysis slides. One of such chemical analysis apparatuses is disclosed in, for example, Japanese Unexamined Patent Publication No. 56(1981)-77746. Also, as a means for analyzing liquid samples automatically and sequentially, there has been proposed in, for example, U.S. Pat. No. 3,526,480 an apparatus wherein a long tape-like test film containing a reagent is accommodated instead of the aforesaid chemical analysis slides, and sample application, incubation and measurement are carried out sequentially by pulling out the test film.

The technique using the chemical analysis slide has the drawback that the chemical analysis slide requires a high manufacturing cost and the running cost of the apparatus is high. Also, with this technique wherein a single chemical analysis slide is used for a single measurement, many chemical analysis slides must be processed for automatically and sequentially carrying out the analysis of liquid samples, and therefore the apparatus becomes complicated, large and expensive. On the other hand, the technique wherein the long tape-like test film is used is advantageous in that the running cost is low and measurement can be carried out automatically and sequentially. However, in the case of an apparatus wherein a sample-applied portion of the long test film is conveyed into an incubator provided at a position different from the sample application and incubated in the incubator after the liquid sample is applied to the test film, the test film must be pulled out over a long length for the purpose of conveyance of the test film into the incubator, and therefore the test film cannot be utilized efficiently. Also, at the time the long test film is to be loaded into the apparatus, it is necessary to carry out the operations of fitting a feed reel around which the unused long test film is wound and a wind-up reel around which no long test film has been wound to the apparatus and winding a leading edge portion of the long test film around the wind-up reel. At the time the long test film is to be discarded after being used, it is necessary to carry out the operations of disengaging the wind-up reel from the apparatus and then removing the feed reel from the apparatus. Such processing of the long test film is troublesome.

SUMMARY OF THE INVENTION

The primary object of the present invention is to provide a biochemical analysis apparatus which is made simple, small and cheap by employing the system utilizing a long tape-like test film advantageous for carrying out measurement automatically and sequentially, and wherein the long test film is utilized efficiently and processing of the long test film is facilitated.

Another object of the present invention is to provide a biochemical analysis apparatus which is made simple, small and cheap by employing the system utilizing a long tape-like test film advantageous for carrying out measurement automatically and sequentially, and wherein the long test film is utilized efficiently, measurement is carried out quickly, and processing of the long test film is facilitated.

The present invention provides a first biochemical analysis apparatus comprising:

i) a sample accommodating means for accommodating a liquid sample, ii) a test film accommodating means for accommodating a long test film containing a reagent which reacts with said liquid sample to give rise to a change in optical density, iii) a test film conveyance means for sequentially pulling out said long test film accommodated in said test film accommodating means, iv) a sample application means for taking up said liquid sample accommodated in said sample accommodating means and applying a predetermined amount of said liquid sample onto said long test film at the position to which said long test film has been pulled out of said test film accommodating means, v) an incubator for maintaining the sample-applied portion of said long test film at a predetermined temperature for a predetermined time, vi) a measurement means for irradiating light to said sample-applied portion of said long test film and measuring the optical density given rise to by said reaction, a cutter for cutting said long test film to a length necessary for a single step of said sample application, said cutter being provided on the side which is upstream from the position of said sample application and where said long test film is conveyed, and a cut-film conveyance means for conveying the sample-applied and cut portion of said long test film into said incubator.

The present invention also provides a second biochemical analysis apparatus comprising:

i) a sample accommodating means for accommodating a plurality of liquid samples, ii) a test film accommodating means provided rotatably in a horizontal plane for accommodating a plurality of long test films, each of which contains a reagent reacting with each of said liquid samples to give rise to a change in optical density, on a circumference having its center at an axis of rotation of said test film accommodating means with leading edges of said long test films facing outward from said circumference, iii) a test film conveyance means for conveying a leading edge portion of the long test film that has been moved to a predetermined position among said long test films accommodated in said test film accommodating means, so that said leading edge portion is exposed outward from said test film accommodating means, iv) a cutter for cutting said exposed leading edge portion of said long test film to form a test film piece, v) a sample application means for taking up one of said liquid samples accommodated in said sample accommodating means and applying a predetermined amount of the liquid sample onto said leading edge portion of said long test film at said predetermined position before said leading edge portion is cut or onto said test film piece, vi) an incubator provided rotatably in a horizontal plane for accommodating a plurality of test film pieces, on which said liquid samples have been applied by said sample application means, on a circumference having its center at an axis of rotation of said incubator, and maintaining said test film pieces at a predetermined temperature for a predetermined time, vii) a measurement means for measuring the optical density of each of said test film pieces during or after the passage of said predetermined time, and viii) a discharging means for discharging said test film piece on which the measurement of the optical density has been finished to the outside of said incubator.

With the first biochemical analysis apparatus for applying the liquid sample onto the long test film, incubating the sample-applied film portion by an incubator, and measuring the degree of color formation at the sample-applied portion by the measurement means, the cutter is provided on the side which is upstream from the position of the sample application and where the long test film is conveyed, and cuts the long test film to a length necessary for a single step of sample application. Therefore, the long test film upstream from the cutter can be used for the subsequent measurements, and can thus be utilized efficiently. Also, at the time the test film is to be loaded to the apparatus, it is only necessary that a feed reel around which the unused test film is wound be set in the apparatus. The test film after being used is discharged in the cut form. Accordingly, the used film portions may be discarded after being accumulated in a predetermined amount, and processing of the test film is facilitated.

Also, in the case where the first biochemical analysis apparatus in accordance with the present invention is constituted so that the incubator has a length capable of accommodating a plurality of the sample-applied and cut test film portions and the sample-applied and cut portions of the long test film are sequentially conveyed by the cut-film conveyance means into the incubator, subsequent operations of sample application can be carried out while the incubation is being carried out, and therefore processing can be carried out sequentially and quickly.

With the second biochemical analysis apparatus in accordance with the present invention, the leading edge portion of the long test film is cut by the cutter to form the test film piece, and the test film piece on which the liquid sample has been applied before or after the test film piece is cut is incubated in the incubator. Therefore, the long test film upstream from the cutter can be used for the subsequent measurements, and can thus be utilized efficiently. Also, with the second biochemical analysis apparatus in accordance with the present invention wherein the incubator is constituted for accommodating a plurality of the test film pieces cut from the long test film, many measurements corresponding to many liquid samples can be carried out sequentially and quickly without the incubation time obstructing the quick processing. Furthermore, at the time the test film is to be loaded to the apparatus, it is only necessary that a feed reel around which the unused test film is wound be set in the apparatus. The test film after being used is discharged in the cut form. Accordingly, the used film portions may be discarded after being accumulated in a predetermined amount, and processing of the test film is facilitated.

DESCRIPTION OF THE PREFERRED EMBODIMENTS

The present invention will hereinbelow be described in further detail with reference to the accompanying drawings.

Figure 1:
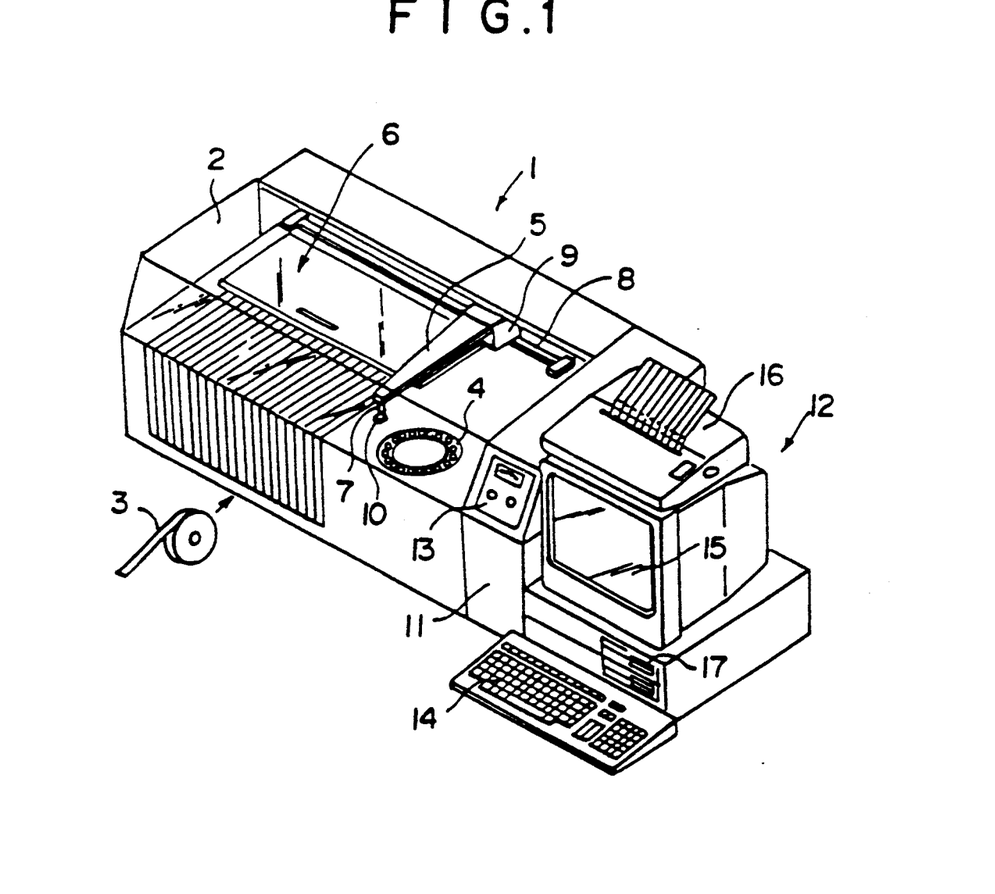
FIG. 1 is a perspective view showing an embodiment of the first biochemical analysis apparatus in accordance with the present invention.

With reference to FIG. 1 showing an embodiment of the first biochemical analysis apparatus in accordance with the present invention, a biochemical analysis apparatus 1 is provided with a transparent cover 2, and a liquid sample, a long tape-like test film 3 and the like are fed into and out of the apparatus 1 by opening the cover 2. The apparatus 1 is provided with a sample accommodating means 4 for accommodating a liquid sample such as blood serum or urine along a ring-like area, and the liquid sample is taken up from the sample accommodating means 4 and applied onto the long test film 3 by a sample application means 5 as will be described later. The long test film 3 contains a reagent undergoing a color reaction with only a specific chemical constituent or a specific physical constituent that is to be analyzed in the liquid sample, and many kinds of the long test films 3, 3, . . . are prepared in accordance with the measurement items. A test film accommodating means 6 accommodates a plurality of the long test films 3, 3, . . . in parallel so that various items of measurements can be carried out simultaneously by use of the apparatus 1. The sample application means 5 is provided with a sample applying nozzle 7 at the end, and is moved in the extending direction of a rail 8 by a movement means 9 placed on the rail 8 for taking up the liquid sample from the sample accommodating means 4, and applying the liquid sample onto the long test film 3 pulled out by a test film conveyance means from the test film accommodating means 6. The movement means 9 also moves the sample application means 5 vertically. The sample application means 5 is kept at its upper position at the time it is moved by the movement means 9 in the extending direction of the rail 8, and is moved down at the time of taking out and application of the liquid sample and at the time of washing as will be described later.

After applying the liquid sample onto the test film, the sample applying nozzle 7 is washed at a nozzle washing region 10 provided close to the test film accommodating means 6 and the sample accommodating means 4 therebetween, and is reused for sample application.

The test film on which the liquid sample has already been applied is incubated by an incubator as will be described later, and subjected to measurement by a measurement means.

Control of operations of the overall apparatus 1, processing of the measurement data and the like are carried out by a circuit region 11 and a computer 12 connected therewith. An operating and display region 13 on the front surface of the circuit region 11 is provided with a power source switch for the apparatus 1, an ammeter for monitoring the current consumption in the apparatus 1, and other members. The computer 12 is provided with a keyboard 14 for giving instructions to the apparatus 1, a CRT display device 15 for displaying the subsidiary information for instructions, measurement results and other items, a printer 16 for printing the measurement results, and a floppy disk drive unit 17 for accommodating a floppy disk for storage of commands for giving various instructions to the apparatus 1 and the information on the measurement results.

Figure 2:
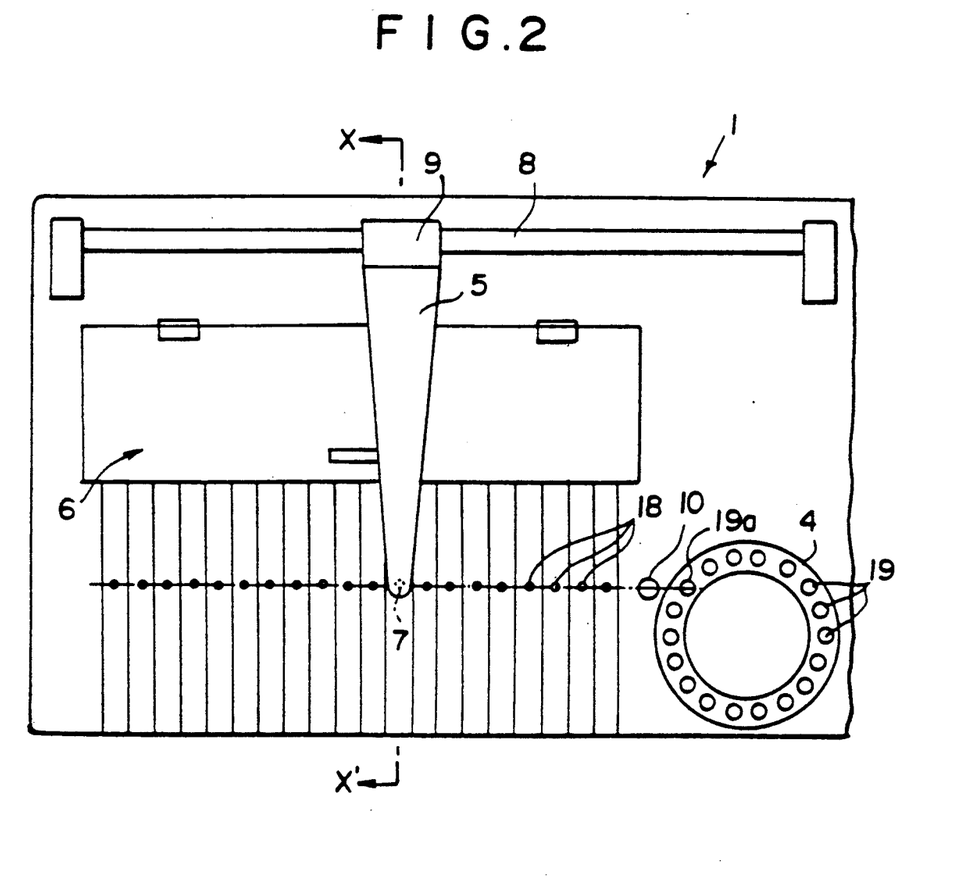
FIG. 2 is a plan view showing the major part of the embodiment shown in FIG. 1.

With reference to FIG. 2 showing the major part of the apparatus 1, the test film accommodating means 6 is constituted so that sample applying positions 18, 18, . . . for all of the test films pulled out of the test film accommodating means 6 stand in a straight line indicated by the chain line. Also, the nozzle washing region 10 and a liquid sample take-out position 19a in the sample accommodating means 4 are disposed on said straight line. The arrangement of the aforesaid positions and the nozzle washing region 10 on the straight line simplifies the configuration of the movement means as will be described later, which in turn contributes to a decrease in operation failures and cost of the apparatus 1.

The sample accommodating means 4 accommodates a plurality of liquid samples in accommodating regions 19, 19, . . . disposed in the ring-like area. The accommodating regions 19, 19, . . . are automatically rotated by a rotation means (not shown) along the circular path until the liquid sample which is accommodated in one of the accommodating regions 19, 19, . . . and which is to be used for the next measurement arrives at the take-out position 19a. In order to prevent the liquid samples accommodated in the accommodating regions 19, 19, . . . from evaporating and deteriorating, a cover (not shown) is provided on the accommodating regions 19, 19, . . . outside of the take-out position 19a.

The sample application means 5 is moved by the movement means 9 in the extending direction of the rail 8, takes up the liquid sample from the take-out position 19a, and applies it to the sample applying position 18 on the test film.

Figure 3:
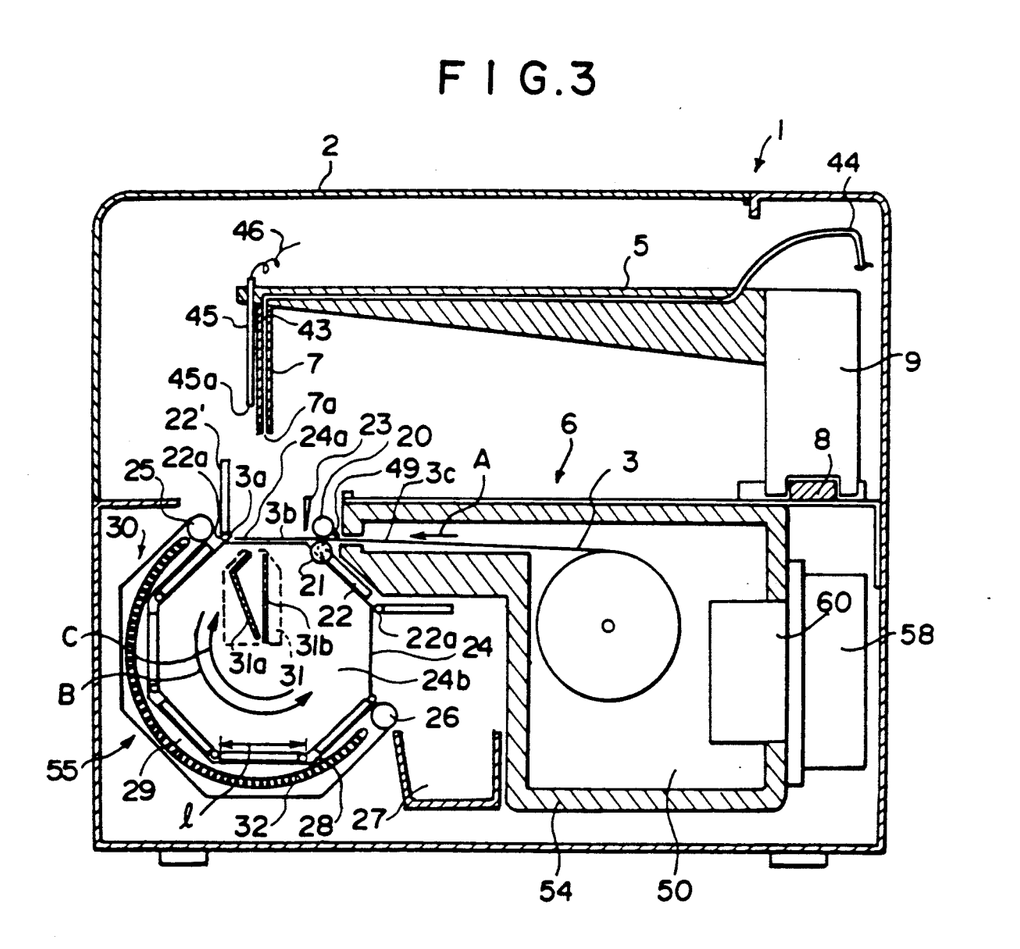
FIG. 3 is a sectional view taken along line X—X' of FIG. 2.

FIG. 3 is a sectional view taken along line X—X' of FIG. 2. In FIG. 3, similar elements are numbered with the same reference numerals with respect to FIGS. 1 and 2.

With reference to FIG. 3, the long test film 3 is wound up and accommodated in a refrigerator 50 constituting the test film accommodating means 6. The refrigerator 50 is enclosed by a refrigerator wall 54 composed of a heat insulating material. A cooling and dehumidifying device 58 for keeping the inside of the refrigerator 50 at a predetermined low temperature and low humidity is provided on one surface of the refrigerator wall 54, and air inside of the refrigerator 50 is circulated by a fan 60.

The portion of the long test film 3 pulled out of a film outlet 49 of the refrigerator 50 passes between rollers 20 and 21 constituting the test film conveyance means. The roller 21 is divided into two parts so that the roller 21 pushes the long test film 3 only at both edge portions and the middle roller portion does not interfere with the passage of an evaporation preventing cover 22 as will be described later. The roller 20 is coupled with a rotation shaft of a motor (not shown). As the motor is operated, the rollers 20 and 21 are rotated to convey the long test film 3 in the direction as indicated by the arrow A. A cutter 23 for cutting the long test film 3 to a length necessary for a single step of sample application is provided in the vicinity of the rollers 20 and 21 on the side downstream from the rollers 20 and 21 as viewed in the direction of conveyance of the long test film 3. When the rollers 20 and 21 are rotated and the long test film 3 is conveyed in the direction as indicated by the arrow A, the portion of the long test film 3 downstream from the cutter 23 is placed on a surface 24a of a regular-polygonal aluminium drum 24, a leading edge 3a of the long test film 3 advances to the vicinity of the downstream corner of the surface 24a (i.e. to the position indicated in FIG. 3), and then the long test film 3 is stopped. A liquid sample is then applied by the sample application means 5 onto a test film 3b thus placed on the surface 24a of the drum 24. Then, the test film 3b placed on the surface 24a of the drum 24 is cut by the cutter 23 and separated from a long test film 3c present on the upstream side.

An elongated pipe 43 continuing into a leading edge 7a of the sample applying nozzle 7 is provided in the sample application means 5. The pipe 43 is communicated with a flexible pipe 44 so that the liquid sample is fed through the pipes 43 and 44 into the sample application means 5 and applied onto the test film 3b. At the time the sample applying nozzle 7 is to be washed, the leading edge 7a of the sample applying nozzle 7 is immersed in a small vessel containing distilled water and provided at the nozzle washing region 10, and washing liquid is delivered from a tank (not shown) through the pipes 43 and 44.

A liquid level detector 45 is provided in parallel with the sample applying nozzle 7 in the vicinity thereof. The liquid level detector 45 is provided so that its leading edge 45a is slightly (for example, by approximately 2.5 mm) higher than the leading edge 7a of the sample applying nozzle 7. When the sample application means 5 is moved down by the movement means 9 for taking up the liquid sample accommodated in the sample accommodating means 4, the leading edge 7a of the sample applying nozzle 7 enters the liquid sample, and the leading edge 45a of the liquid level detector 45 contacts the liquid sample. At this time, a signal indicating that the leading edge 45a of the liquid level detector 45 has contacted the liquid sample is produced by the liquid level detector 45, and transmitted to the circuit region 11 shown in FIG. 1 through a signal line 46. Based on the signal, the downward movement of the sample application means 5 is stopped. In this manner, the leading edge 7a of the sample applying nozzle 7 can be entered into the liquid sample up to a predetermined depth from the surface of the liquid sample regardless of the amount of the liquid sample.

The sample application may be carried out prior to the cutting in the manner as mentioned above, or the cutting may be carried out prior to the sample application.

The drum 24 constituting a cut-film conveyance means is rotated by a rotation means (not shown) in the direction as indicated by the arrow B. As the drum 24 is thus rotated, an evaporation preventing cover 22' coupled with the drum 24 via a coil spring 22a contacts a cylindrical member 25 and is thus brought down onto the cut test film 3b. The cut test film 3b is thus held by the cover 22' and is moved in the direction as indicated by the arrow B.

Each of evaporation preventing covers 22, 22, . . . (including the aforesaid evaporation preventing cover 22') formed of a material having high thermal conductivity such as aluminium is joined to the vicinity of each of the corners of the drum 24 via the coil spring 22a, and is urged to a position opened at an angle of approximately 90° with respect to each surface of the drum 24. Upon receiving external force, the evaporation preventing cover 22 is brought down and one surface thereof contacts the surface of the drum 24. The evaporation preventing cover 22 pushes the test film 3b against the surface of the drum 24 and prevents the liquid sample applied onto the test film 3b from evaporating.

An endless belt 28 is provided in the region close to the drum 24 between the cylindrical member 25 and a cylindrical member 26 provided in the vicinity of a test film discarding region 27. The evaporation preventing cover 22 is pushed by the endless belt 28 and thus continues to hold the test film 3b between the cylindrical members 25 and 26. The face in the region more outward than the endless belt 28 between the cylindrical members 25 and 26 and regions on both sides of said face are surrounded by a material such as aluminium. In this manner, a cover member 30 having a hollow region 29 therein and covering the drum 24 is formed. A heater 32 for maintaining the test film 3b at a predetermined temperature is provided in the hollow region 29 and maintains an inside 24b of the drum 24 at the predetermined temperature. An incubator 55 is constituted by the drum 24, the cover member 30 and the heater 32. The incubator 55 is constituted to sequentially accommodate a plurality of test films 3b, 3b, . . . as shown in FIG. 3.

A glass window is provided in each surface of the drum 24 at the position corresponding to the sample-applied portion of the test film 3b. A measurement means 31 is reciprocally rotated in the directions as indicated by the arrows B and C, irradiates light projected by a light projecting fiber 31a to the test film 3b through the glass window of the drum 24, and receives the light reflected by the test film 3b by use of a light receiving fiber 31b. In this manner, the measurement means 31 measures the background, i.e. the optical reflection density of the test film 3b without the liquid sample applied thereon, and the optical density of the test film 3b, on which the liquid sample has already been applied, during or after the incubation.

When the drum 24 is rotated and the test film 3b on which the incubation and measurement have been finished goes beyond the cylindrical member 26, holding of the evaporation preventing cover 22 is released, and the evaporation preventing cover 22 is rotated to the position approximately normal to the surface of the drum 24. As a result, the test film 3b is released from holding and is accommodated in the test film discarding region 27.

An embodiment of the second biochemical analysis apparatus in accordance with the present invention will hereinbelow be described with reference to FIGS. 4, 5A and 5B.

Figure 4:
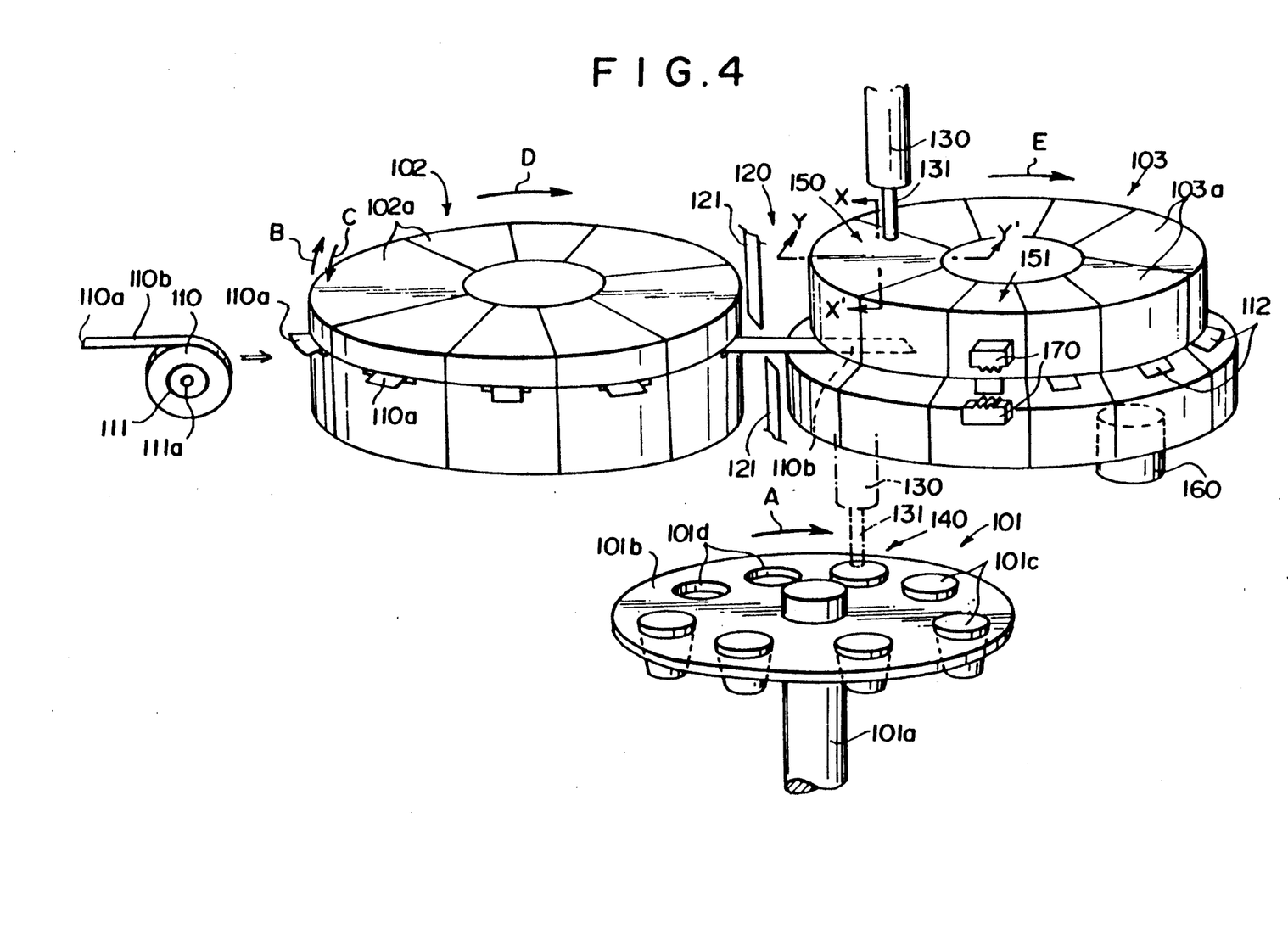
FIG. 4 is a perspective view showing an embodiment of the second biochemical analysis apparatus in accordance with the present invention.

With reference to FIG. 4 showing the major part of the embodiment of the second biochemical analysis apparatus in accordance with the present invention, a sample accommodating means 101 for accommodating a plurality of liquid samples has a rotation shaft 101a rotated by a motor (not shown) As the rotation shaft 101a is rotated, a rotatable table 101b is rotated in the direction as indicated by the arrow A. The rotatable table 101b is provided with holes 101d, 101d, . . . adapted to the shapes of sample cups 101c, 101c, . . . so that a plurality of the sample cups 101c, 101c, . . . are located along a circular region. Each of the sample cups 101c, 101c, . . . accommodates a liquid sample such as serum and is positioned in the each of the holes 101d, 101d, . . . of the rotatable table 101b. In this manner, a plurality of the liquid samples are accommodated in the sample accommodating means 101, and the liquid sample which is to be used for the next measurement is located at a predetermined position 140.

A plurality of long test films 110, 110, . . . giving rise to a change in the optical density upon reaction with the liquid sample are accommodated in a test film accommodating means 102. One of covers 102a, 102a, . . . is raised in the direction as indicated by the arrow B, and the long test film 110 is accommodated so that a hole 111a at the center of a feed reel 111 around which the long test film 110 is wound engages with a shaft of a motor (not shown) constituting a test film conveyance means inside of the test film accommodating means 102 and a leading edge 110a of the long test film 110 faces outward and is slightly exposed to the outside. Then, the cover 102a is closed in the direction as indicated by the arrow C. The test film accommodating means 102 is rotatable in the direction as indicated by the arrow D, and a leading edge portion 110b of the long test film 110 moved to a predetermined position 120 is conveyed and exposed outward by the motor (not shown) constituting the test film conveyance means. In this embodiment, the outwardly-exposed leading edge portion 110b of the long test film 110 is directly inserted into an incubator 103 as will be described later.

After the leading edge portion 110b of the long test film 110 has been inserted into the incubator 103, the leading edge portion 110b of the long test film 110 is cut and separated from the long test film 110 by a cutter 121 provided between the test film accommodating means 102 and the incubator 103. In this manner, a test film piece 112 is formed.

The incubator 103 has a nearly cylindrical shape and is constituted to accommodate a plurality of the test film pieces 112, 112, ... on the circumference to maintain them at a predetermined temperature for a predetermined time. The incubator 103 is rotatable in the direction as indicated by the arrow E.

A sample application means 130 has a sample applying nozzle 131 at the end and is moved to the position above the sample accommodating means 101 (i.e. to the position as indicated by the chain line in FIG. 4). The sample applying nozzle 131 is then moved down, and the lower edge thereof is immersed in the liquid sample contained in the sample cup 101c at the predetermined position 140. Thereafter, the liquid sample is sucked up from the lower edge of the sample applying nozzle 131 by a suction means (not shown). After the suction is completed, the sample applying nozzle 131 is moved up, the sample application means 130 is moved to a sample applying position 150 as indicated by the solid line in FIG. 4, and a predetermined amount of the liquid sample is delivered and applied from the sample applying nozzle 131 onto the leading edge portion 110b of the long test film 110 before being cut or onto the test film piece 112 after being cut.

Figure 5A:
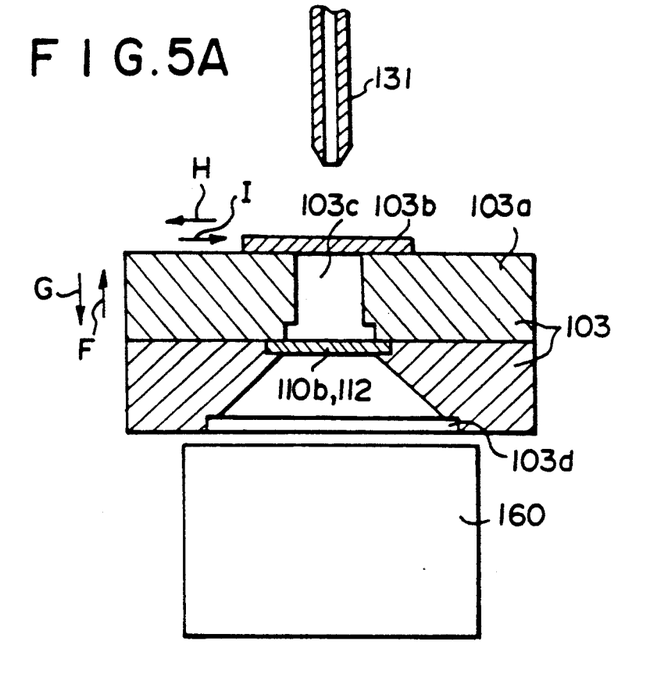
FIGS. 5A and 5B are sectional views taken along lines X—X' and Y—Y' of FIG. 4.
Figure 5B:
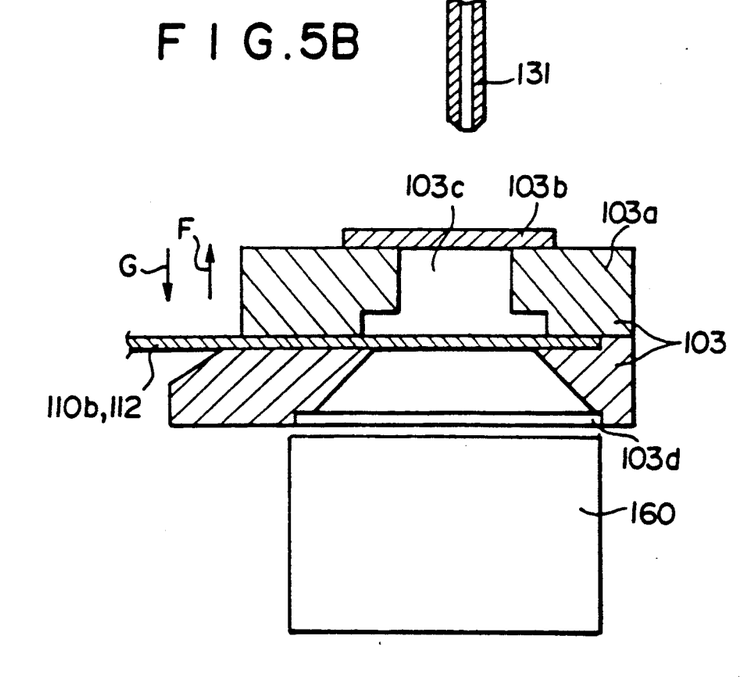

FIGS. 5A and 5B are sectional views taken along lines X—X' and Y—Y' of FIG. 4 respectively. In FIGS. 5A and 5B, similar elements are numbered with the same reference numerals with respect to FIG. 4 and with respect to each other.

The leading edge portion 110b of the long test film 110 is conveyed by the test film conveyance means from the rear of the drawing sheet in FIG. 5A to the front thereof, exposed out of the test film accommodating means 102 shown in FIG. 4, and inserted into the incubator 103. At the time the leading edge portion 110b of the long test film 110 is to be thus inserted into the incubator 103, an upper cover 103a of the incubator 103 is moved in the direction as indicated by the arrow F. After the leading edge portion 110b of the long test film 110 has been inserted into the incubator 103, the upper cover 103a is moved in the direction as indicated by the arrow G and pushes the leading edge portion 110b of the long test film 110 as shown in FIG. 5A. Thereafter, a shutter 103b is moved in the direction as indicated by the arrow H in FIG. 5A, the sample applying nozzle 131 is moved down to apply the liquid sample onto the leading edge portion 110b of the long test film 110 through a hole 103c. The shutter 103b is then moved in the direction as indicated by the arrow I to close the hole 103c and prevent air from flowing between the hole 103c and the exterior. In this manner, the sample-applied portion of the long test film 110 is incubated at a predetermined temperature (for example, 37° C.). The lower part of the incubator 103 is closed by a transparent glass plate 103d.

After the sample application is finished, the leading edge portion 110b of the long test film 110 is cut by the cutter 121 shown in FIG. 4, and the test film piece 112 is thus formed. The sample application may thus be carried out prior to the cutting, or may be carried out after the test film piece 112 is formed by the cutting by use of the cutter 121. As shown in FIG. 4, one edge portion of the test film piece 112 is exposed outward from the incubator 103.

After the sample application and the cutting are finished, the incubator 103 is rotated in the direction as indicated by the arrow E in FIG. 4, and the test film accommodating means 102 are rotated when necessary in the direction as indicated by the arrow D in FIG. 4. The next leading edge portion 110b of the long test film 110 or the leading edge portion 110b of the next long test film 110 is then inserted into the incubator 103, and the sample application and the cutting are repeated.

A measurement means 160 for measuring the optical density of the sample-applied portion of the test film piece 112 accommodated in the incubator 103 is provided below the incubator 103. The measurement means 160 is moveable along the circumference having its center at the axis of rotation of the incubator 103 for measuring the optical density of the sample-applied portions of a plurality of the test film pieces 112, 112, ... accommodated in the incubator 103. In this manner, the measurement of the optical density of the sample-applied portion of the test film piece 112 is carried out during or after the incubation. The measurement means 160 is moveable also to the position below the sample applying position 150 shown in FIG. 4 for measuring the background, i.e. the optical reflection density of the leading edge portion 110b of the long test film 110 without the liquid sample applied thereon or of the test film piece 112 without the liquid sample applied thereon.

The measurement means 160 need not necessarily be moved. Instead, the incubator 103 may be rotated in the direction as indicated by the arrow E in FIG. 4 and/or reversely until the test film piece 112 which is to be measured faces the measurement means 160, and the optical density or the background of the test film piece 112 may thus be measured.

After the test film piece 112 on which the measurement has been finished is moved to a discharging position 151 shown in FIG. 4, the upper cover 103a of the incubator 103 is moved up, i.e. in the direction as indicated by the arrow F in FIG. 5A, to release the test film piece 112. The test film piece 112 thus released is grasped by a discharging means 170, pulled out of the incubator 103, and thrown away into a box (not shown).

The aforesaid operations are sequentially repeated quickly, and the measurement is carried out quickly for many measurement items for many liquid samples.

We claim:

1. A biochemical analysis apparatus, comprising:
   i) a sample accommodating means for storing a liquid sample,
   ii) a test film accommodating means for housing a plurality of elongated, continuous test films in a side-by-side relationship, each containing a reagent which reacts with said liquid sample to give rise to a change in optical density, iii) a test film conveyance means for sequentially pulling out said elongated, continuous test films housed in said test film accommodating means and linearly conveying said elongated, continuous test films to a sample application position, iv) a sample application means for taking up said liquid sample stored in said sample accommodating means and applying a predetermined amount of said liquid sample onto at least one of said elongated, continuous test films at the sample application position to which said elongated, continuous test film has been pulled out of said test film accommodating means, wherein said elongated, continuous test films are positioned in a single horizontal plane perpendicular to the direction in which said predetermined amount of said liquid sample is applied to said at least one of said elongated, continuous test films, v) an incubator for maintaining the sample-applied portion of said elongated, continuous test film at a predetermined temperature for a predetermined time, and vi) a measurement means for irradiating light to said sample-applied portion of said elongated, continuous test film and measuring the optical density given rise to by said reaction, said measurement means being positioned in said incubator, a cutter for cutting said elongated, continuous test film to a length necessary for a single step of said sample application, said cutter being positioned between said sample application means and said test film accommodating means, said incubator including a cut-film conveyance means for conveying the sample-applied and cut portion of said elongated, continuous test film through said incubator, said cut-film conveyance means including a cover which prevents evaporation of said liquid sample during incubation and measuring, said cover being coupled to said cut-film conveyance means and being conveyed thereby so as to cover said sample-applied and cut portion of said elongated, continuous test film as said cut-film conveyance means conveys said cut and sample-applied portion through said incubator, wherein said sample application position is located in said incubator.

2. An apparatus as defined in claim 1 wherein said cut-film conveyance means comprises a drum-shaped member for supporting said sample-applied and cut portion of said elongated, continuous test film thereon and rotatable for conveying said sample-applied and cut portion of said elongated, continuous test film into said incubator.

3. An apparatus as defined in claim 2 wherein said incubator is constituted by said drum-shaped member, a cover member having a hollow region therein and covering said drum-shaped member, and a heater provided in said hollow region.

4. A biochemical analysis apparatus according to claim 1, wherein said cut-film conveyance means comprises a plurality of springs and a rotatable drum for supporting said sample-applied and cut portion of said test film thereon, said rotatable drum having a plurality of corners with a spring corresponding to each corner, and a cover being coupled to said rotatable drum at each of said plurality of corners by said corresponding spring which urges said spring in a direction away from said rotatable drum, wherein said cover is moved downwardly to cover said sample-applied and cut portion of said elongated, continuous test film to prevent evaporation of said liquid sample as said rotatable drum is rotated.

5. A biochemical analysis apparatus according to claim 1, wherein said measurement means is reciprocally rotatable and comprises a light projecting fiber and a light receiving fiber, said cut-film conveyance means having a window formed therein such that said light projecting fiber irradiates light through said window to said test film, wherein said light receiving fiber receives light reflected by said test film.

6. A biochemical analysis apparatus, comprising:
i) a sample accommodating means for storing a plurality of liquid samples,
ii) a test film accommodating means provided rotatably in a horizontal plane for housing a plurality of elongated, continuous test films, each of which contains a reagent reacting with each of said liquid samples to give rise to a change in optical density on a circumference having its center at an axis of rotation of said test film accommodating means with leading edges of said elongated, continuous test film facing outward from said circumference,
iii) a test film conveyance means for linearly conveying a leading edge portion of the elongated, continuous test film that has been moved to a predetermined position among said elongated, continuous test films housed in said test film accommodating means, so that said leading edge portion is exposed outward from said test film accommodating means,
iv) a cutter for cutting said exposed leading edge portion of said elongated, continuous test film to form a test film piece,
v) a sample application means for taking up one of said liquid samples stored in said sample accommodating means and applying a predetermined amount of the liquid sample onto said leading edge portion of said elongated, continuous test film at said predetermined position before said leading edge portion is cut or onto said test film piece,
vi) an incubator provided rotatably in a horizontal plane for accommodating a plurality of test film pieces, on which said liquid samples have been applied by said sample application means, on a circumference having its center at an axis of rotation of said incubator, and maintaining said test film pieces at a predetermined temperature for a predetermined time so as to incubate said plurality of test film pieces simultaneously,
vii) a measurement means for measuring the optical density of each of said test film pieces during or after the passage of said predetermined time, and
viii) a discharging means for discharging said test film piece on which the measurement of the optical density has been finished to the outside of said incubator, wherein said sample application position is in said incubator.

7. An apparatus as defined in claim 6 wherein said measurement means is rotatable along said circumference having it center at the axis of rotation of said incubator.

8. A biochemical analysis apparatus according to claim 6, wherein said incubator includes an opening through which said sample application means applies said liquid sample to said elongated, continuous test film, and means for preventing air flow between a position inside of said incubator and a position outside of said incubator, said air flow preventing means being reciprocally movable to cover said opening.

* * * * *